United States Patent [19]

Ogata et al.

[11] Patent Number: 4,595,780

[45] Date of Patent: Jun. 17, 1986

[54] SULFONAMIDO-BENZAMIDE DERIVATIVES

[75] Inventors: Masaru Ogata; Kosaburo Sato, both of Hyogo; Takao Konishi, Osaka, all of Japan

[73] Assignee: Shionogi & Co., Ltd., Osaka, Japan

[21] Appl. No.: 568,072

[22] Filed: Jan. 4, 1984

[51] Int. Cl.$^4$ .................................... C07C 161/00
[52] U.S. Cl. ........................................... 564/79
[58] Field of Search ......................... 564/79, 91, 99

[56] References Cited

U.S. PATENT DOCUMENTS 3,178,339  4/1965  Frick et al. ........................ 564/99

FOREIGN PATENT DOCUMENTS 369441   5/1963  Switzerland ...................... 564/99
2078215  1/1982  United Kingdom .

Primary Examiner—Charles F. Warren
Assistant Examiner—R. A. Picard
Attorney, Agent, or Firm—Birch, Stewart, Kolasch & Birch

[57] ABSTRACT

Novel sulfonamide benzamides which have potent antiviral and anti-coccidial activities with low toxicity and compositions containing them used in prophylaxis or treatment of viral infectious diseases or coccidiosis are provided.

9 Claims, No Drawings

SULFONAMIDO-BENZAMIDE DERIVATIVES

BACKGROUND OF THE INVENTION

1. Field of the Invention

The present invention relates to benzamides of the sulfonamide-type which exhibit potent antiviral and anti-coccidial activities.

2. Description of the Prior Art

Several antiviral and anti-coccidial compounds are commercially available. The known antiviral agents, for example, enviroxime and zinviroxime (U.S. Pat. No. 4,118,742) which are somewhat structurally related to the compounds of the present invention, however, are expected to be used in very limited viral infections because of their problems with stability, solubility, side effects, and toxicity. Some sulfonamide-type compounds exhibiting antibacterial activity accompanied with anti-coccidial activity can be exemplified by sulfabenz and sulfanitran, while they have no antiviral activity.

BRIEF SUMMARY OF THE INVENTION

The present invention relates to benzamides of sulfonamide-type. More particularly, it relates to the compounds represented by the following formula (I):

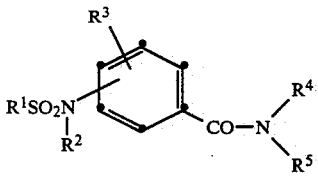

(I)

wherein $R^1$ is a $C_1$–$C_5$ alkyl, phenyl, $C_2$–$C_{10}$ dialkylamino group, or a 5- or 6-membered heterocyclic residue; $R^2$ is hydrogen, a $C_1$–$C_5$ alkyl, or phthalidyl group; $R^3$ is hydrogen, halogen, a $C_1$–$C_5$ alkyl, or $C_1$–$C_5$ alkoxy group; $R^4$ is $C_1$–$C_5$ alkyl group which may be substituted by 1 or 2 phenyl or furyl groups, a $C_3$–$C_6$ cycloalkyl group, a phenyl group which may have a condensed benzene ring or 1 or 2 substituents, or a 5- or 6-membered heterocyclic residue; and $R^5$ is hydrogen or a $C_1$–$C_5$ alkyl group.

The objective compounds (I) can be prepared according to Routes A, B, and C as mentioned in the detailed description of the invention.

The compounds (I) are useful as antiviral agents and they can be administered orally or parenterally to humans or other animals. Furthermore, the compounds (I) can also be used as anti-coccidial agents.

DETAILED DESCRIPTION OF THE INVENTION

The present invention relates to benzamides of the sulfonamide-type. More particularly, it relates to the compounds represented by the following formula (I):

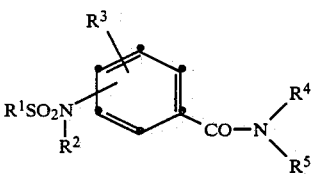

(I)

wherein $R^1$ is a $C_1$–$C_5$ alkyl, phenyl, $C_2$–$C_{10}$ dialkylamino group, or 5- or 6-membered heterocyclic residue; $R^2$ is hydrogen, a $C_1$–$C_5$ alkyl, or phthalidyl group; $R^3$ is hydrogen, halogen, a $C_1$–$C_5$ alkyl, or $C_1$–$C_5$ alkoxy group; $R^4$ is a $C_1$–$C_5$ alkyl group which may be substituted by 1 or 2 phenyl or furyl groups, a $C_3$–$C_6$ cycloalkyl group, a phenyl group which may have a condensed benzene ring or 1 or 2 substituents, or a 5- or 6-membered heterocyclic residue; and $R^5$ is hydrogen or a $C_1$–$C_5$ alkyl group.

The meanings of the terms used in the above definition are shown below: the $C_1$–$C_5$ alkyl group includes methyl, ethyl, n-propyl, isopropyl, n-butyl, isobutyl, sec-butyl, tert-butyl, n-pentyl, sec-pentyl, neo-pentyl, tert-pentyl, and the like, among which the $C_1$–$C_3$ alkyl group is preferred in the definition of $R^2$ and $R^5$; the $C_2$–$C_{10}$ dialkylamino group includes dimethylamino, methylethylamino, methylpropylamino, diethylamino, methylbutylamino, ethylpropylamino, ethylbutylamino, dipropylamino, ethylpentylamino, propylbutylamino, dibutylamino, propylpentylamino, butylpentylamino, propylhexylamino, dipentylamino, butylhexylamino, among which the $C_2$–$C_6$ dialkylamino group is preferred; the 5- or 6-membered heterocyclic residue includes pyrrolidinyl, piperidinyl, morpholino, and the like in the definition of $R^1$, and that in the definition of $R^4$ is pyridyl, pyrimidinyl, thiazolyl, oxazolyl, isoxazolyl, and the like; the halogen includes fluorine, chlorine, bromine, iodine, and the like; the $C_1$–$C_5$ alkoxy includes methoxy, ethoxy, n-propoxy, isopropoxy, n-butoxy, isobutoxy, tert-butoxy, n-pentyloxy, sec-pentyloxy, neo-pentyloxy, tert-pentyloxy, and the like; the $C_1$–$C_5$ alkyl which may be substituted by 1 or 2 phenyl or furyl groups includes tert-butyl, benzyl, diphenylmethyl, furylmethyl, and the like; the $C_3$–$C_6$ cycloalkyl includes cyclopropyl, cyclobutyl, cyclopentyl, cyclohexyl, and the like; in the definition of the phenyl which may have a condensed benzene ring or 1 or 2 substituents, the substituents include a $C_1$–$C_6$ alkyl group (e.g. methyl, ethyl, n-propyl, isopropyl, n-butyl, isobutyl, tert-butyl, n-pentyl, sec-pentyl, neo-pentyl, tert-pentyl, n-hexyl, and the like), a $C_1$–$C_5$ alkoxy group (e.g. methoxy, ethoxy, n-propoxy, isopropoxy, n-butoxy, isobutoxy, tertbutoxy, n-pentyloxy, sec-pentyloxy, neo-pentyloxy, tert-pentyloxy, and the like), halogen, trifluoromethyl, alkanoyl (e.g. formyl, acetyl, propionyl, butyryl, valeryl, and the like), alkoxycarbonyl (e.g. methoxycarbonyl, ethoxycarbonyl, propoxycarbonyl, butoxycarbonyl, pentyloxycarbonyl), carbamoyl, phenyl, hydroxy, hydroxymethyl, nitro, amino, cyano, and the like. Examples of the phenyl group which may have a condensed benzene ring or 1 or 2 substituents are phenyl, naphthyl, halo-phenyl (e.g. 2-fluorophenyl, 4-fluorophenyl, 2-chlorophenyl, 3-chlorophenyl, 4-chlorophenyl, 4-bromophenyl, 4-iodophenyl, 3,4-dichlorophenyl), $C_1$–$C_6$ alkyl-phenyl (e.g. 3-methylphenyl, 4-methylphenyl, 4-ethylphenyl, 4-n-propylphenyl, 4-isopropylphenyl, 4-n-butylphenyl, 4-isobutylphenyl, 4-tert-butylphenyl, 4-n-pentylphenyl, 4-sec-pentylphenyl, 4-n-hexylphenyl), $C_1$–$C_5$ alkoxy-phenyl (e.g. 3-methoxyphenyl, 4-methoxyphenyl, 4-n-propoxyphenyl), 3-trifluoromethylphenyl, 4-trifluoromethylphenyl, alkanoylphenyl (e.g. 2-acetylphenyl, 4-acetylphenyl), alkoxycarbonyl-phenyl (e.g. 3-methoxycarbonylphenyl, 4-methoxycarbonylphenyl), 3-carbamoylphenyl, 2-biphenylyl, 3-hydroxyphenyl, 3-hydroxymethylphenyl, 3-nitrophenyl, 2-aminophenyl, 4-cyanophenyl, and the like.

The objective compounds (I) can be prepared according to Routes A, B, and C as shown below.

Route A

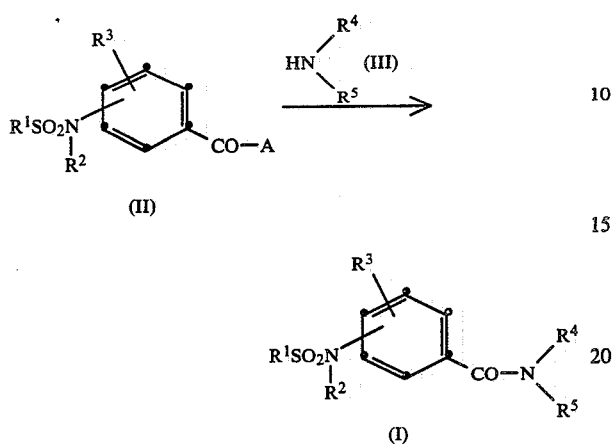

(I)

wherein A is hydroxy or a reactive group (e.g. halogen, tosyloxy, active ester residue such as alkoxycarbonyloxy); $R^1$, $R^2$, $R^3$, $R^4$, and $R^5$ are each as defined above.

In this route, the objective compounds (I) are prepared from the benzoic acids or reactive derivatives thereof (II) on the amidation with the amines (III). The amidation is carried out in an appropriate solvent (e.g. benzene, toluene, methylene chloride, dimethylformamide, tetrahydrofuran, acetone, acetonitrile), if necessary, in the presence of a base (e.g. triethylamine, pyridine, picolines) at a temperature of about 0° C. to about 150° C., preferably room temperature (e.g. 15°-25° C.) or an elevated temperature up to about 80° C. When the free benzoic acid is used as a starting material, the reaction may be carried out in the above mentioned solvent at a temperature of about 0° C. to about 50° C. in the presence of a condensing agent such as DCC (dicyclohexylcarbodiimide), and the like in a conventional manner.

The starting materials (II) can be provided by reacting the corresponding aminobenzoic acids (VII) with sulfonating agents (V) and then if necessary, converting the resulting free carboxylic acids into the reactive derivatives as described above. The reaction sequence can be depicted as follows.

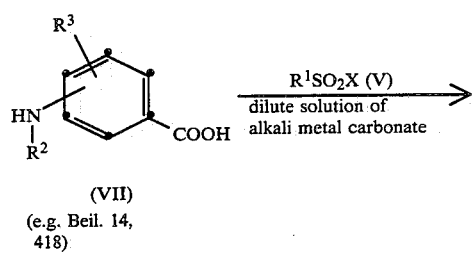

(VII)
(e.g. Beil. 14, 418)

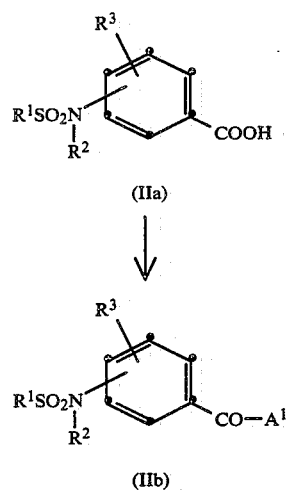

(wherein $A^1$ is reactive group; X is halogen; $R^1$, $R^2$, and $R^3$ are as defined above).

Route B

The objective compounds (I) wherein $R^2$ is hydrogen, i.e. compounds (Ia) can be prepared according to the Route B as shown below.

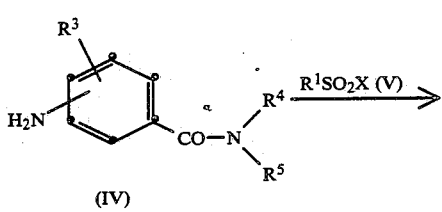

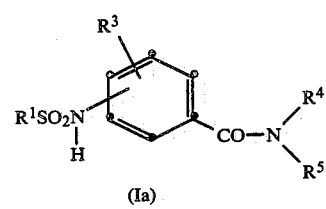

(Ia)

wherein X, $R^1$, $R^3$, $R^4$, and $R^5$ are each as defined above.

In this route, the sulfonamide formation from the anilines (IV) into the compounds (Ia) is achieved by the reaction with sulfonating agents (V) in a conventional manner. The reaction is generally conducted in an appropriate solvent (e.g. dimethylformamide, chloroform, tetrahydrofuran, acetonitrile, acetone, water, and the like) at a temperature of about 0° C. to about 100° C., preferably room temperature in the presence of an inorganic or organic base (e.g. sodium hydroxide, triethylamine, pyridine, picolines, and the like). The organic base, for example, pyridine also works as a solvent.

The starting materials (IV) may be provided by amidation of the corresponding nitrobenzoic acids (VIII) and subsequent reduction of the nitro groups to amino groups as described below.

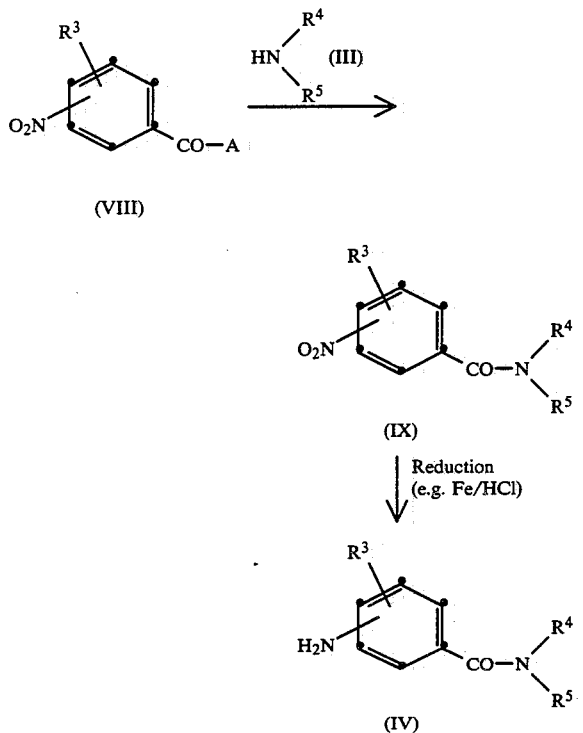

wherein A, $R^3$, $R^4$, and $R^5$ are each as defined above.

Route C

The compounds (I) wherein $R^2$ is not hydrogen, i.e. compounds (Ib) can be prepared from the compounds (Ia) by an alkylation or phthalidyl formation reaction.

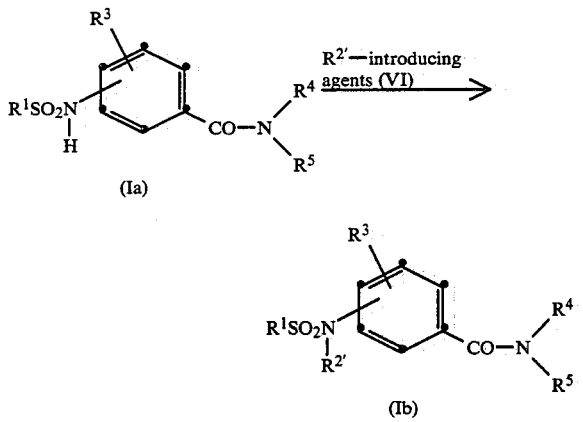

wherein $R^1$, $R^3$, $R^4$, and $R^5$ are as defined above; $R^{2'}$ is defined as $R^2$ with proviso that $R^{2'}$ is not hydrogen.

The reaction is generally conducted with $R^{2'}$-introducing agents (VI), i.e. alkylating agents (e.g. methyl iodide, butyl bromide, dimethyl sulfate), or phthalidylating agents (e.g. 3-chlorophthalide, 3-bromophthalide, and the like) in an appropriate solvent (e.g. acetone, dioxane, acetonitrile, dimethylformamide, dimethylsulfoxide, chloroform, methylene chloride, and the like) at a temperature of about 30° C. to about 200° C., preferably, 50° C. to 100° C. in the presence of an inorganic or organic base (e.g. sodium carbonate, potassium hydroxide, triethylamine, pyridine, picolines).

Effects and Uses

The compounds (I) of the present invention exhibit an antiviral activity for humans and other animals. They have a potent proliferation inhibiting activity against rhino virus, polio virus, and coxsackie virus and are useful as antiviral agents. For example, 4'-bromo-4-[(dimethylaminosulfonyl)amino]benzanilide and 4'-n-butyl-4-[(dimethylaminosulfonyl)amino]benzanilide showed $ED_{50}$ 0.27 μg/ml and 0.07 μg/ml respectively in test by a plaque reduction method according to the modified Siminoff method as described in Applied Microbiology, 9, (1), 66 (1961). The other compounds have shown the same antiviral activity as the compounds described above.

The compounds (I) of the present invention can be administered orally or parenterally to humans or other animals as antiviral agents and can be formulated with pharmaceutically acceptable diluents (e.g. starch, sucrose, calcium carbonate, kaolin), extenders (e.g. lactose, starch, calcium phosphate, kaolin, bentonite, talc), lubricants (e.g. magnesium stearate, sodium benzoate), disintegrators (e.g. starch, agar, carboxymethyl cellulose, sodium alginate), and/or other excipients in a conventional manner. These formulations can be exemplified by an aqueous solution, suspension, powder, granules, capsules, tablets, dry syrup, injection, suppositories, nasal drop, nasal cavity spray, and the like.

The compounds of the present invention may be orally administered to humans in a single dose or divided doses of 0.1-80 mg/kg per day in the treatment of viral infections.

Furthermore, the compounds (I) of the present invention are useful as anti-coccidial agents for poultry, exhibiting excellent anti-coccidial activities against Eimeria tenella, Eimeria acervulina or the like. For example, 4'-chloro-4-[(dimethylaminosulfonyl)amino]benzanilide showed high relative weight gain, no excretion of bloody feces and practically no cecal lesions with 100% survival, when 400 ppm of the compound in feed was given to broiler chickens from 8 days of age, the next day the chickens were orally inoculated with $5 \times 10^4$ sporulated oocysts of Eimeria tenella per chicken, and on the 6 th day the chickens were weighed and killed for observation of cecal lesions. Poultry coccidiosis due to Eimeria tenella or Eimeria acervulina usually causes bleeding in the digestive organs, death, and growth inhibition in poultry such as chickens, turkeys, or ducks. The heretofore used anti-coccidial agents including sulfa drugs, nitrofurans, quinolines, anti-thiamine agents, benzamides and antibiotic substances, however, suffer from some drawbacks in their degree of the anti-coccidial activity, their toxicity or intolerance by the hosts, and the emergence of resistant strains owing to misuse of the drugs over a long period. Such factors have gradually decreased the value of the known drugs. Advantages of the present invention consist in that the compounds (I) have a low toxicity to host poultry, and induce no or negligible drug resistance in target organisms.

For poultry anti-coccidial compositions comprising the compounds (I), suitable formulations which may be used, include powder, granules, solution, dispersion, premix, capsule, emulsion, and tablets, alone or in combination with an appropriate carrier common to this field. There can be combined ordinary additives including vehicles, disintegrating agents, lubricants, and coating materials. In general, a suitable concentration of the compounds (I) for poultry feed is at least 0.003 weight percent. For prophylactic use, a suitable concentration of the compounds (I) is about 0.003 to about 0.06 weight percent, more favorably about 0.003 to about 0.02 weight percent, and for therapeutic purposes a suitable concentration is about 0.01 weight percent to about 0.16 weight percent. For instance, a solution, suspension or emulsion may be used in combination with drinking water; capsules or tablets may be administered orally as they are. By carriers is meant a diluent substance to be ordinarily added into poultry feed and involves illustratively water, lactose, sucrose, talc, pectin, wheat powder, rice bran, wheat bran, corn powder, soy bean meal, crushed grain powder and the like. The present anti-coccidial compositions may optionally be used in combination with animal drugs including antibiotics, other known poultry anti-coccidial agents, anthelmintics, and the like.

The present invention will be explained in more detail by examples and preparation of starting materials. Examples of the present invention are described below.

EXAMPLE 1

Preparation of 4'-bromo-4-isopropanesulfonamidebenzanilide 3

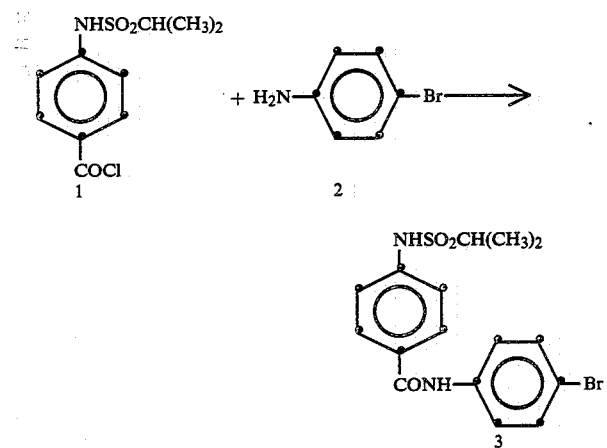

A mixture of 250 mg of 4-isopropanesulfonamidobenzoylchloride 1, 181 mg of 4-bromoaniline 2, 106 mg of triethylamine, and 5 ml of methylene chloride is stirred at room temperature for 5 minutes. The reaction mixture is neutralized with a sodium bicarbonate solution, and extracted with methylene chloride. The organic layer is concentrated under reduced pressure, and the residue is chromatographed on a column of silica-gel. The eluate with 3% methanolmethylene chloride is concentrated, and the residue is crystallized from ethyl acetate-isopropyl ether. The crude resulting crystals are recrystallized from ethyl acetateisopropyl ether to give 200 mg of 4'-bromo-4-isopropanesulfonamidobenzanilide 3 as pure specimen, m.p. 213°–214° C.

Elemental Analysis (for $C_{16}H_{17}N_2O_3SBr$): Calcd. (%): C, 48.37; H, 4.31; N, 7.05; S, 8.07; Br, 20.11. Found (%): C, 48.48; H, 4.20; N, 6.92; S, 8.15 Br, 20.37.

EXAMPLE 2

Preparation of 4-[(dimethylaminosulfonyl)amino]benzanilide 6

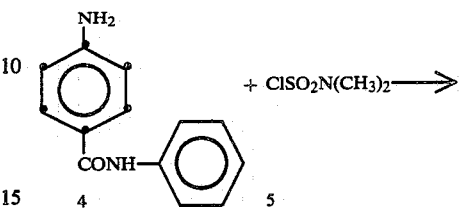

[Grammaticakis, Compt. Rend., 259 (23), 4295–8 (1964)]

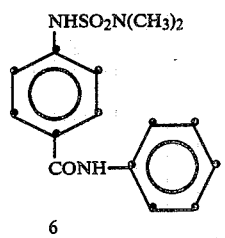

To a solution of 1.0 g of 4-aminobenzanilide 4 dissolved in 10 ml of dried pyridine is added 1.01 g of dimethylaminosulfonyl chloride 5 at room temperature, and the mixture is stirred over-night. The reaction mixture is poured into ice-water, acidified with 6N hydrochloric acid, and extracted with a mixture of methylene chloride-methanol. The organic layer is extracted again with 10% sodium hydroxide solution. The alkaline layer is acidified with 6N hydrochloric acid; the precipitate is collected by filtration and recrystallized from methanol to give 864 mg of 4-[(dimethylaminosulfonyl)amino]benzanilide 6 as crystals, m.p. 213°–215° C.

Elemental Analysis (for $C_{15}H_{17}N_3O_3S$): Calcd. (%): C, 56.41; H, 5.37, N, 13.16; S, 10.04. Found (%): C, 56.46; H, 5.23; N, 13.13; S, 10.08.

EXAMPLE 3

Preparation of 4'-chloro-4-[methyl(dimethylaminosulfonyl)amino]benzanilide 9

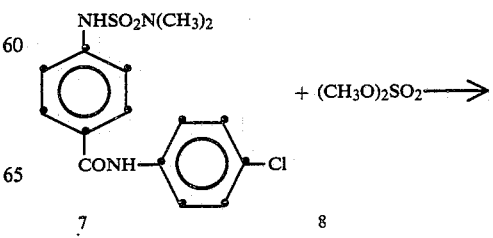

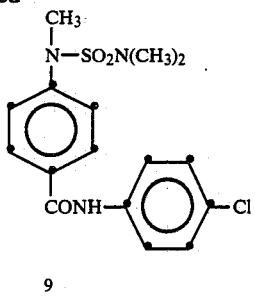

9

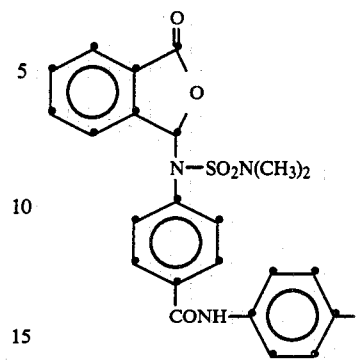

12

A mixture of 300 mg of 4'-chloro-4-[(dimethylaminosulfonyl)amino]benzanilide 7, 140 mg of potassium carbonate, 130 mg of dimethyl sulfate 8, and 10 ml of dried acetone is refluxed for 30 minutes. Acetone is distilled off from the reaction mixture, the residue is basified with 10% sodium hydroxide solution and extracted with methylene chloride. The organic layer is washed with water, dried over anhydrous sodium sulfate, and concentrated. The residue is crystallized from ethyl acetate-isopropyl ether to give 300 mg of 4'-chloro-4-[methyl(dimethylaminosulfonyl)amino]benzanilide 9 as crystals, m.p. 155°–156° C.

Elemental Analysis (for $C_{16}H_{18}N_3O_3ClS$): Calcd. (%): C, 52.24; H, 4.93; N, 11.42; Cl, 9.64; S, 8.72. Found (%): C, 52.12; H, 4.82; N, 11.27; Cl, 9.71; S, 8.68.

EXAMPLE 4

Preparation of 4'-bromo-4-[(dimethylaminosulfonyl)(3-phthalidyl)amino]benzanilide 12

To a solution of 1.0 g of 4'-bromo-4-[(dimethylaminosulfonyl)amino]benzanilide 10 and 10 ml of dried acetone are added 416 mg of potassium carbonate powder and 642 mg of 3-bromophthalide 11, and the mixture is refluxed for 1 hour. The reaction mixture is concentrated; to the residue is added water, and the precipitating crystals are collected by filtration and recrystallized from acetonitrile to give 680 mg of 4'-bromo-4-[(dimethylaminosulfonyl)(3-phthalidyl)amino]benzanilide 12 as crystals, m.p. 244°–245.5° C.

EXAMPLES 5–78

The following objective compounds (Ia) can be prepared by the reaction of the starting materials (II) with (III) in the same manner as in Example 1.

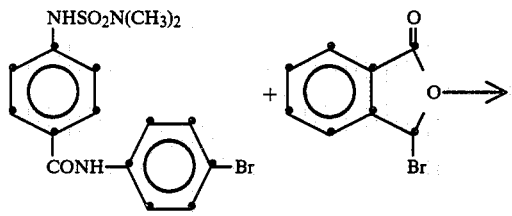

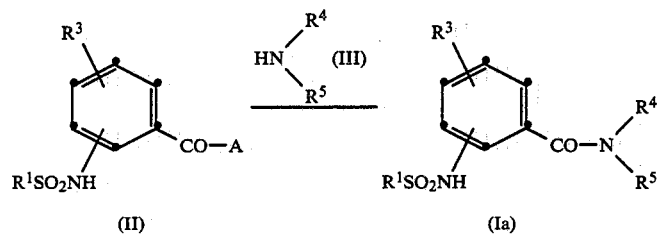

| Ex. Nos. | *$R^1$ | $R^3$ | $R^4$ | $R^5$ | mp(°C.)/IR(cm$^{-1}$) |
|---|---|---|---|---|---|
| 5 | 3-Me$_2$N | H | Ph | H | 140–141.5 |
| 6 | " | " | 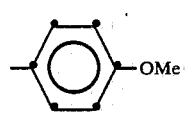 | " | 123–124 |

-continued $$\underset{\text{(II)}}{\underset{R^1SO_2NH}{\underset{\|}{\bigcirc}}\!\!\!\!\!\!\!\!\!\!\!\!\!\!\!\!\!\!\!\!\!\!\!-CO-A} \quad \underset{R^5}{\overset{R^4}{\underset{|}{HN}}}\text{(III)} \quad \longrightarrow \quad \underset{\text{(Ia)}}{\underset{R^1SO_2NH}{\underset{\|}{\bigcirc}}\!\!\!\!\!\!\!\!\!\!\!\!\!\!\!\!\!\!\!\!\!\!\!-CO-N\underset{R^5}{\overset{R^4}{\diagdown}}}$$

| Ex. Nos. | *R¹ | R³ | R⁴ | R⁵ | mp(°C.)/IR(cm⁻¹) |
|---|---|---|---|---|---|
| 7 | " | " | 4-Me-C₆H₄ with CN | " | oil, 2220, 1680 CHCl₃ |
| 8 | (3) pyrrolidin-1-yl | " | Ph | " | 146–147 |
| 9 | (3) piperidin-1-yl | " | " | " | 110–111 |
| 10 | 3-Me | " | " | " | 177–178 |
| 11 | 3-Ph | " | " | " | 159–160 |
| 12 | 3-Me₂N | " | 4-Me-C₆H₄-Ph | " | oil, 3410, 3000 1680 CHCl₃ |
| 13 | " | " | 4-Me-C₆H₄-Cl | " | 127–128 |
| 14 | 3-i-Pr | " | Ph | " | amor., 3420, 3350 1670, CHCl₃ |
| 15 | " | " | 4-Me-C₆H₄-OH | " | 171.5–172 |
| 16 | " | " | 4-Me-2,3-Cl₂-C₆H₃ | " | 184–185.5 |
| 17 | " | " | 4-Me-C₆H₄-COOMe | " | 158–159 |
| 18 | " | " | 4-Me-C₆H₄-CONH₂ | " | 137–139 |
| 19 | 2-Me₂N | " | " | " | 123–125 |

-continued
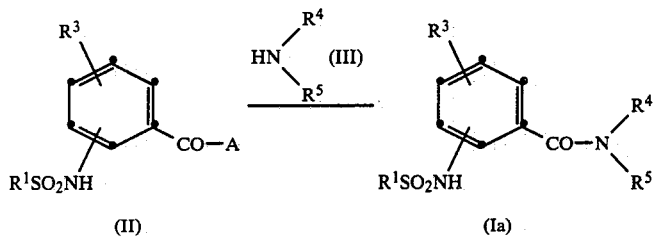
| Ex. Nos. | *R¹ | R³ | R⁴ | R⁵ | mp(°C.)/IR(cm⁻¹) |
|---|---|---|---|---|---|
| 20 | 3-i-Pr | " | 2-Me-C₆H₄-COMe | " | 163–164 |
| 21 | " | " | 2-Me-C₆H₄-NO₂ | " | 173–173.5 |
| 22 | " | " | 2-Me-C₆H₄-NH₂ | " | 130–131 |
| 23 | " | " | 2-Me-C₆H₄-CH₂OH | " | amor., 3000, 1670 CHCl₃ |
| 24 | " | " | 2-Me-C₆H₄-Cl | " | 146–147 |
| 25 | " | " | 2-Me-C₆H₄-COOMe | " | 157–158 |
| 26 | 3-Me₂N | " | 2-Me-C₆H₄-COOMe | " | 150–151 |
| 27 | 3-i-Pr | " | 2-Me-C₆H₄-Cl (4-Cl) | " | 151–152 |
| 28 | " | " | 2-Me-C₆H₄-Cl (3-Cl) | " | amor., 3410, 3370 1685, CHCl₃ |

-continued
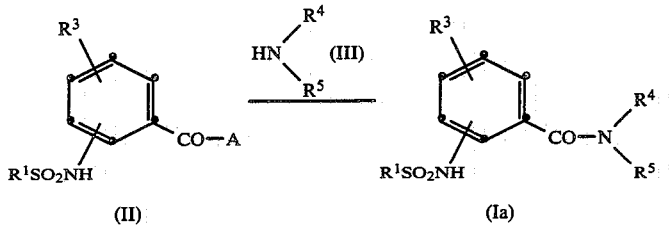
| Ex. Nos. | *R¹ | R³ | R⁴ | R⁵ | mp(°C.)/IR(cm⁻¹) |
|---|---|---|---|---|---|
| 29 | 4-Me₂N | " | 4-Cl-C₆H₄ (2-Me) | " | 228–229 |
| 30 | " | " | 4-Cl-C₆H₄ (3-Me) | " | 223–224 |
| 31 | " | " | 3-Cl-C₆H₄ (2-Me) | " | 190–192 |
| 32 | 4-i-Pr | " | 4-Cl-C₆H₄ (2-Me) | " | 214–215 |
| 33 | " | " | 4-Me-C₆H₄ (2-Me) | " | 177–178 |
| 34 | 4-Me₂N | " | 4-Me-C₆H₄ (2-Me) | " | 199–200 |
| 35 | " | " | 4-OMe-C₆H₄ (2-Me) | " | 182–183 |
| 36 | 4-i-Pr | " | 4-OMe-C₆H₄ (2-Me) | " | 188–189 |
| 37 | 4-Me₂N | " | 4-COMe-C₆H₄ (2-Me) | " | 197.5–198.5 |
| 38 | " | " | 4-COOMe-C₆H₄ (2-Me) | " | 202–203 |
| 39 | 3-Me₂N | 4-Cl | Ph | " | 147–149 |

-continued
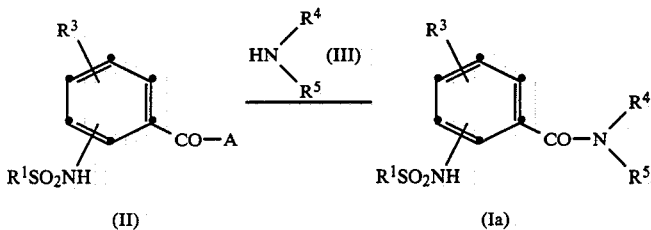
| Ex. Nos. | *R¹ | R³ | R⁴ | R⁵ | mp(°C.)/IR(cm⁻¹) |
|---|---|---|---|---|---|
| 40 | 4-i-Pr | H | 4-F-phenyl | " | 236–237 |
| 41 | " | " | 3-F-phenyl | " | 134–135 |
| 42 | " | " | 2-CH₃-phenyl | " | 116 |
| 43 | 3-i-Pr | " | 4-Br-phenyl | " | 147.5–148.5 |
| 44 | " | " | 4-F-phenyl | " | 146–147 |
| 45 | 3-Me₂N | 6-Cl | 4-Cl-phenyl | " | 157–158 |
| 46 | 3-i-Pr | 6-MeO | " | " | 149–150 |
| 47 | 4-Me₂N | H | 4-Br-phenyl | " | 217–218 |
| 48 | 4-i-Pr | " | 4-Cl-phenyl | " | 212–213 |
| 49 | 4-Me₂N | " | 2-CF₃-phenyl | " | 222–223 |
| 50 | 3-Me₂N | " | " | " | 136–136.5 |

-continued

|   | | R⁴ | | |
|---|---|---|---|---|
| | | HN (III) | | |
| | | R⁵ | | |

(II) R³-phenyl-CO-A with R¹SO₂NH → (Ia) R³-phenyl-CO-N(R⁴)(R⁵) with R¹SO₂NH

| Ex. Nos. | *R¹ | R³ | R⁴ | R⁵ | mp(°C.)/IR(cm⁻¹) |
|---|---|---|---|---|---|
| 51 | 4-Me₂N | " | 4-CF₃-phenyl | " | 227–228 |
| 52 | " | " | 4-Et-phenyl | " | 207–208 |
| 53 | 3-Me₂N | " | 4-CF₃-phenyl | " | 175–176 |
| 54 | 4-i-Pr | " | " | " | 226.5–227.5 |
| 55 | 4-Me₂N | " | 4-i-Pr-phenyl | " | 194–195 |
| 56 | " | " | 4-I-phenyl | " | 215–216 |
| 57 | 3-Me₂N | " | pyridyl | " | 143–145 |
| 58 | " | " | pyrimidinyl | " | 102–103 |
| 59 | " | " | naphthyl | " | 177–178 |
| 60 | " | " | phenyl | " | 184–185 |
| 61 | 3-i-Pr | " | thiazolyl | " | 216–217 |
| 62 | " | " | t-Bu | " | 3000, 1670, CHCl₃ |
| 63 | " | " | —CH(Ph)₂ | " | 225–227 |

-continued
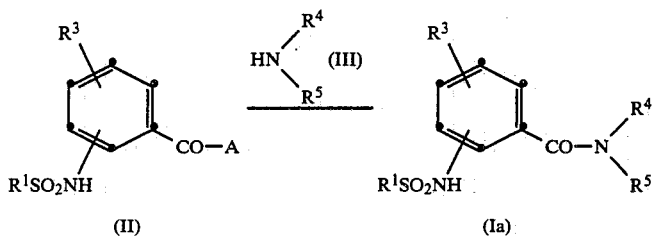
(II)  (III)  (Ia)
| Ex. Nos. | *R¹ | R³ | R⁴ | R⁵ | mp(°C.)/IR(cm⁻¹) |
|---|---|---|---|---|---|
| 64 | " | " | —CH₂—(furan) | " | 135.5–136.5 |
| 65 | " | " | —CH₂—Ph | " | 158.5–159.5 |
| 66 | " | " | Ph | Me | 167–168 |
| 67 | 4-Me₂N | " | —C₆H₄—Cl | " | 188–189 |
| 68 | " | " | —C₆H₄—n-Bu | H | 171–172 |
| 69 | 3-Me₂N | " | —C₆H₄—Br | " | 164–166 |
| 70 | 4-Me₂N | " | —C₆H₄—n-Pe | " | 148–149 |
| 71 | " | " | —C₆H₄—O—Pr | " | 195–196 |
| 72 | " | " | —C₆H₄—n-Pr | " | 184–186 |
| 73 | " | " | —C₆H₄—n-He | " | 155–156 |
| 74 | " | " | —C₆H₄—t-Bu | " | 201–202 |
| 75 | " | " | —C₆H₄—i-Bu | " | 188–190 |

-continued

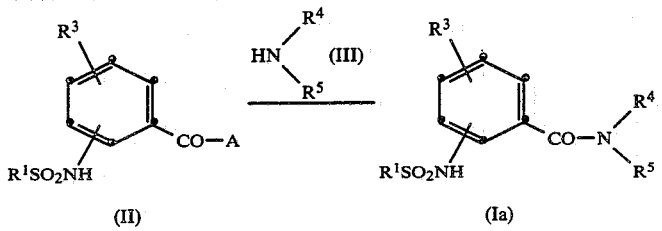

| Ex. Nos. | *R¹ | R³ | R⁴ | R⁵ | mp(°C.)/IR(cm⁻¹) |
|---|---|---|---|---|---|
| 76 | 4-i-Pr | " | —⟨phenyl⟩—n-Bu | " | 181–182 |
| 77 | 4-Me₂N | " | —⟨phenyl⟩—sec-Pe | " | 138–139 |
| 78 | 3-i-Pr | " | —⟨phenyl⟩—n-Bu | " | 122–123 |

Note:
*The number attached to the group defined by R¹ represents the location on the benzene ring. The abbreviations have the following significance. Me (methyl), Et (ethyl), Pr (propyl), Bu (butyl), Pe (pentyl), He (hexyl), Ph (phenyl), amor. (amorphous powder)

EXAMPLES 79–80

In the same manner as in Example 3, the following objective compounds can be prepared by methylation.

| Ex. Nos. | Structural formulae | Chemical names | m.p. (°C.) |
|---|---|---|---|
| 79 | CH₃<br>│<br>NSO₂CH₃<br>⟨benzene⟩<br>CH₃O    CONH—⟨phenyl⟩ | 2-Methoxy-5-(N—methyl-methanesulfonamido)-benzanilide | 151–152 |
| 80 | CH₃<br>│<br>NSO₂N(CH₃)₂<br>⟨benzene⟩<br>CONH—⟨phenyl⟩—Cl | 4'-Chloro-3-[methyl-(dimethylamino-sulfonyl)-amino]benz-anilide | 155–156 |

PREPARATION OF STARTING MATERIALS 1

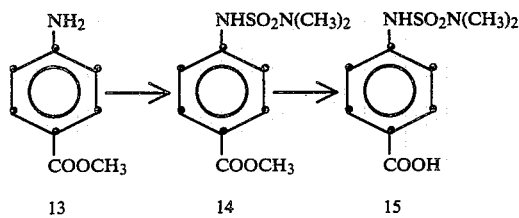

To a solution of 8.5 g of methyl 4-aminobenzoate 13 and 43 ml of pyridine is added 12.1 g of dimethylsulfamoyl chloride, and the mixture is stirred at 50° C. for 2 hours. The reaction mixture to which is added ice-water is acidified with 6N hydrochloric acid and extracted with methylene chloride. The organic layer is washed with water, dried, and concentrated under reduced pressure. The residue is washed with ether-isopropyl ether to give 9.5 g (yield: 65.4%) of methyl 4-(dimethylaminosulfonyl)aminobenzoate 14.

To the above crystalline product is added 48 ml of 10% sodium hydroxide solution. The mixture is heated on a water bath for 5 minutes and acidified with 6N hydrochloric acid. The precipitating crystals are collected by filtration, dried under air, and recrystallized from ethyl acetate-isopropyl ether to give 7.4 g of 4-(dimethylaminosulfonyl)aminobenzoic acid 15.
  m.p. 171°–173° C.
  Yield: 82.4%

When this compound is used as the starting material of the present invention, it is appropriate to use the acid chloride prepared by heating with thionyl chloride.

PREPARATION OF STARTING MATERIALS 2

In the same manner as in the Preparation of starting materials 1, 3-(dimethylaminosulfonyl)aminobenzoic acid can be prepared as crystals, m.p. 183°–185° C.

PREPARATION OF STARTING MATERIALS 3

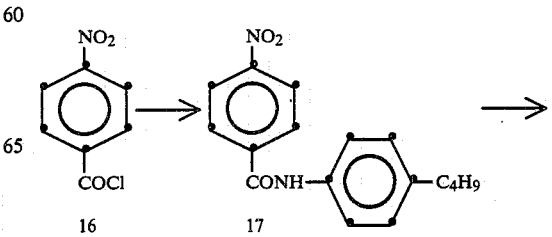

-continued

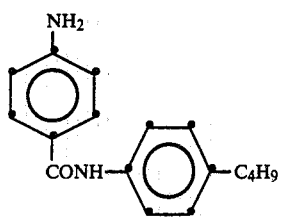

18

To a mixture of 8.04 g of 4-butylaniline, 6.53 g of triethylamine, and 100 ml of dried methylene chloride is dropwise added 10 g of benzoyl chloride to give 4-nitrobenzoyl chloride 16. The mixture is stirred at room temperature for 5 minutes, then poured into a diluted sodium bicarbonate aqueous solution and extracted with methylene chloride. The organic layer is dried over anhydrous sodium sulfate, and concentrated under reduced pressure. The residue is washed with isopropyl ether-ethyl acetate to give 14.0 g of 4'-butyl-4-nitrobenzanilide 17 as crystals, m.p. 151°–152° C.

To a solution of 10 g of the above product and 100 ml of tetrahydrofuran are added 7.96 g of tin and 50 ml of 6N hydrochloric acid, and the mixture is stirred at 50° C. for 1 hour. The reaction mixture is filtered, and the filtrate is concentrated under reduced pressure. The residue is basified with 10% sodium hydroxide solution, and the precipitating crystals are dissolved in methylene chloride. The solution is dried over anhydrous sodium sulfate and concentrated under reduced pressure. The residue is washed with isopropyl ether to give 8.1 g of 4'-butyl-4-aminobenzanilide 18 as crystals, m.p. 137.5°–138.5° C.

PREPARATION OF STARTING MATERIALS 4–8

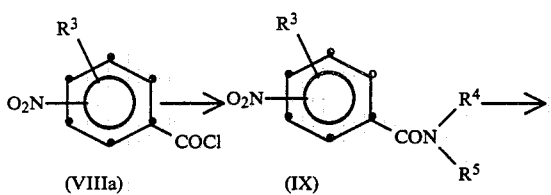

(VIIIa)     (IX)

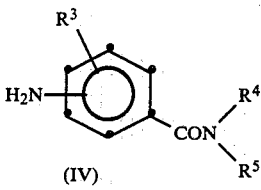

(IV)

In the same manner as in the Preparation of starting materials 3, the following compounds (IX) and (IV) can be prepared.

| Nos. | VIIIa Position of nitro group | IX R³ | R⁴ | R⁵ | m.p. (°C.) | IV m.p. (°C.) |
|---|---|---|---|---|---|---|
| 4 | 3 | H | Ph | H | 149–150 | 121–122 |
| 5 | 4 | H | Ph | H | 216–218 | 137–139 |
| 6 | 2 | H | Ph | H | 146 | 131 |
| 7 | 4 | H | –C₆H₄–Me | H | 202–203 | 166 |
| 8 | 4 | H | –C₆H₄–Br | H | 247 | 206–208 |

What we claim is:
1. A compound of the formula:

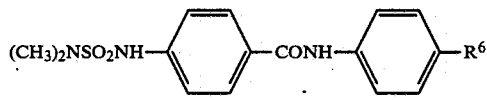

wherein $R^6$ is a member selected from the group consisting of n-propyl, isopropyl, n-butyl, isobutyl, t-butyl, sec-pentyl, n-hexyl, and bromine.

2. A compound claimed in claim 1, namely 4'-n-propyl-4-[(dimethylaminosulfonyl)amino]benzanilide.
3. A compound claimed in claim 1, namely 4'-isopropyl-4-[(dimethylaminosulfonyl)amino]benzanilide.
4. A compound claimed in claim 1, namely 4'-n-butyl-4-[(dimethylaminosulfonyl)amino]benzanilide.
5. A compound claimed in claim 1, namely 4'-isobutyl-4-[(dimethylaminosulfonyl)amino]benzanilide.
6. A compound claimed in claim 1, namely 4'-t-butyl-4-[(dimethylaminosulfonyl)amino]benzanilide.
7. A compound claimed in claim 1, namely 4'-sec-pentyl-4-[(dimethylaminosulfonyl)amino]benzanilide.
8. A compound claimed in claim 1, namely 4'-n-hexyl-4-[(dimethylaminosulfonyl)amino]benzanilide.
9. A compound claimed in claim 1, namely 4'-bromo-4-[(dimethylaminosulfonyl)amino]benzanilide.

* * * * *